United States Patent [19]
Matsuzaki et al.

[11] Patent Number: 5,776,196
[45] Date of Patent: Jul. 7, 1998

[54] PROSTHESIS FOR SPANNING A SPACE FORMED UPON REMOVAL OF AN INTERVERTEBRAL DISK

[75] Inventors: Hiromi Matsuzaki; Satoshi Ojima; Masashi Nakamura, all of Tokyo, Japan

[73] Assignee: Asahi Kogaku Kogyo Kabushiki Kaisha, Tokyo, Japan

[21] Appl. No.: 610,835

[22] Filed: Mar. 5, 1996

Related U.S. Application Data

[62] Division of Ser. No. 306,430, Sep. 19, 1994, Pat. No. 5,534,031, which is a continuation of Ser. No. 9,916, Jan. 27, 1993, abandoned.

[30] Foreign Application Priority Data

Jan. 28, 1992 [JP] Japan .................................. 4-038566

[51] Int. Cl.⁶ .................................................. A61F 2/44
[52] U.S. Cl. ................................................ 623/17; 606/61
[58] Field of Search ................................ 623/17; 606/61

[56] References Cited

U.S. PATENT DOCUMENTS

| | | | |
|---|---|---|---|
| Re. 31,865 | 4/1985 | Roux . | |
| 1,017,371 | 2/1912 | Beck . | |
| 3,848,276 | 11/1974 | Martinez . | |
| 4,044,170 | 8/1977 | Scharbach et al. | 427/2.27 |
| 4,113,500 | 9/1978 | Ebihara et al. . | |
| 4,149,894 | 4/1979 | Ebihara et al. . | |
| 4,230,455 | 10/1980 | Hidaka et al. . | |
| 4,484,570 | 11/1984 | Sutter et al. | 606/72 |
| 4,743,256 | 5/1988 | Brantigan | 623/17 |
| 4,798,585 | 1/1989 | Inoue et al. . | |
| 4,904,257 | 2/1990 | Mori et al. . | |
| 4,919,751 | 4/1990 | Sumita et al. . | |
| 4,946,378 | 8/1990 | Hirayama et al. . | |
| 4,961,740 | 10/1990 | Ray et al. . | |
| 4,969,913 | 11/1990 | Ojima . | |
| 5,015,247 | 5/1991 | Michelson . | |
| 5,017,518 | 5/1991 | Hirayama et al. . | |
| 5,082,803 | 1/1992 | Sumita . | |
| 5,128,146 | 7/1992 | Hirayama et al. . | |
| 5,147,361 | 9/1992 | Ojima et al. . | |

FOREIGN PATENT DOCUMENTS

| | | | |
|---|---|---|---|
| 0188954 | 6/1985 | European Pat. Off. . | |
| 2651992 | 3/1991 | France | 623/17 |
| 3729600 | 3/1989 | Germany . | |
| 4109941 | 10/1992 | Germany . | |
| 1519677 | 11/1989 | U.S.S.R. | 623/17 |
| 8502535 | 7/1986 | WIPO . | |
| 9106266 | 5/1991 | WIPO . | |

*Primary Examiner*—David H. Willse
*Attorney, Agent, or Firm*—Greenblum & Bernstein, P.L.C.

[57] ABSTRACT

An artificial vertebra spacer is embedded in and bridges a space between two adjacent vertebrae which are positioned superiorly and inferiorly of a removed intervertebral disk, respectively. The artificial vertebra spacer includes a hollow cylindrical member, and a helical screw thread disposed integrally on and extending helically around the hollow cylindrical member. A substantially rectangular flange portion is provided at one end of the hollow cylindrical member. The flange portion is provided with at least one hole through which at least one screw passes to fix the spacer.

8 Claims, 9 Drawing Sheets

1

PROSTHESIS FOR SPANNING A SPACE FORMED UPON REMOVAL OF AN INTERVERTEBRAL DISK

This application is a division of application Ser. No. 08/306,430, filed Sep. 19, 1994, now U.S. Pat. No. 5,534,031, which is a continuation of application Ser. No. 08/009,916, filed Jan. 27, 1993, now abandoned.

The present disclosure relates to subject matter contained in Japanese patent application No. 4-38566 (filed on Jan. 28, 1992) which is expressly incorporated herein by reference in its entirety.

BACKGROUND OF THE INVENTION

1. Field of the Invention

The present invention relates to an artificial spacer for keeping adjacent vertebrae spaced from each other after a faulty intervertebral disk has been removed from cervical vertebrae or lumbar vertebrae of a vertebral column.

2. Description of the Relevant Art

In a known surgical procedure to be carried out on a patient who is suffering a spinal failure such as the herniation of an intervertebral disk. The faulty intervertebral disk is removed anteriorly of the patient, and a vertebra filler or spacer is inserted between the vertebrae that are positioned above and below the removed intervertebral disk.

Vertebra fillers that are known for use in the above procedure include autografts taken from the patient's iliac bones, and to bioceramic bones allografts of alumina, hydroxy apatite, or the like.

According to the above medical operation, confronting portions of the vertebrae positioned superiorly and interiorly of the removed intervertebral disk are cut off, and the vertebra spacer is inserted between the vertebrae from the anterior side of the patient, filling up the space between the vertebrae. The vertebra filler is effective to hold the vertebrae in position against compressive forces applied thereto. However, it is less effective to hold the vertebrae in position when tensile forces or forces normal to the compressive or tensile forces are applied thereto.

SUMMARY OF THE INVENTION

It is therefore an object of the present invention to provide an artificial vertebra spacer which is capable of holding adjacent vertebrae stably in position against compressive and tensile forces and also forces normal to the compressive and tensile forces.

According to the present invention, there is provided an artificial vertebra spacer comprising a hollow member adapted to be embedded in two adjacent vertebrae which are positioned superiorly and interiorly a removed intervertebral disk, respectively with respective confronting portions of the vertebrae being positioned within the hollow member, the hollow member being made of a material having a predetermined degree of mechanical strength and rigidity.

According to another aspect of the present invention, there is also provided an assembly comprising an artificial vertebra spacer comprising a hollow member adapted to be embedded in two adjacent vertebrae which are positioned superiorly and inferiorly a removed intervertebral disk, with respective confronting portions of the vertebrae being positioned within the hollow member, the hollow member being made of a material having a predetermined degree of mechanical strength and rigidity, and a plate connected to an end of the artificial vertebra spacer which is exposed on the vertebrae when the hollow member is embedded in the vertebrae. The hollow member may be of a cylindrical shape and have a helical screw thread on an outer circumferential surface, the helical screw thread having screw holes defined therein parallel to an axis of the hollow member, the plate being of an annular shape having an outside diameter which is substantially the same as the outside diameter of the helical screw thread, further comprising at least one screw extending through the plate and threaded into the screw holes defined in the helical screw thread, thereby fastening the plate to the artificial vertebra spacer.

According to still another aspect of the present invention, there is provided an artificial vertebra spacer for being embedded in and bridging a space between two adjacent vertebrae which are positioned superiorly and inferiorly a removed intervertebral disk, respectively the artificial vertebra spacer comprising a hollow cylindrical member, and a helical screw thread disposed integrally on and extending helically around the hollow cylindrical member, each of the hollow cylindrical member and the helical screw thread being made of a metallic material and having a surface layer made of a biocompatible material.

According to yet still another aspect of the present invention, there is provided an assembly comprising an artificial vertebra spacer for being embedded in and bridging a space between two adjacent vertebrae which are positioned superiorly and inferiorly a removed intervertebral disk, respectively the artificial vertebra spacer comprising a hollow cylindrical member, and a helical screw thread disposed integrally on and extending helically around the hollow cylindrical member, an annular plate having a tubular member fitted in an axial end of the artificial vertebra spacer and a circular flange extending radially outwardly from the tubular member, and at least one screw for fastening the circular flange to the helical screw thread when the artificial vertebra spacer is embedded in the vertebrae.

Each of the artificial vertebra spacer, the annular plate, and the at least one screw may be made of a titanium alloy.

According to yet still another aspect of the present invention, there is provided an artificial vertebra spacer comprising a hollow cylindrical member adapted to be embedded in two adjacent vertebrae, screw means, provided on an outer circumferential surface of the hollow cylindrical member, for connecting the hollow cylindrical member with the two adjacent vertebrae, and fixing means for fixing the hollow cylindrical member to the vertebrae.

The above and further objects, details and advantages of the present invention will become apparent from the following detailed description of preferred embodiments thereof, when read in conjunction with the accompanying drawings.

DETAILED DESCRIPTION OF THE PREFERRED EMBODIMENTS

Figure 1:
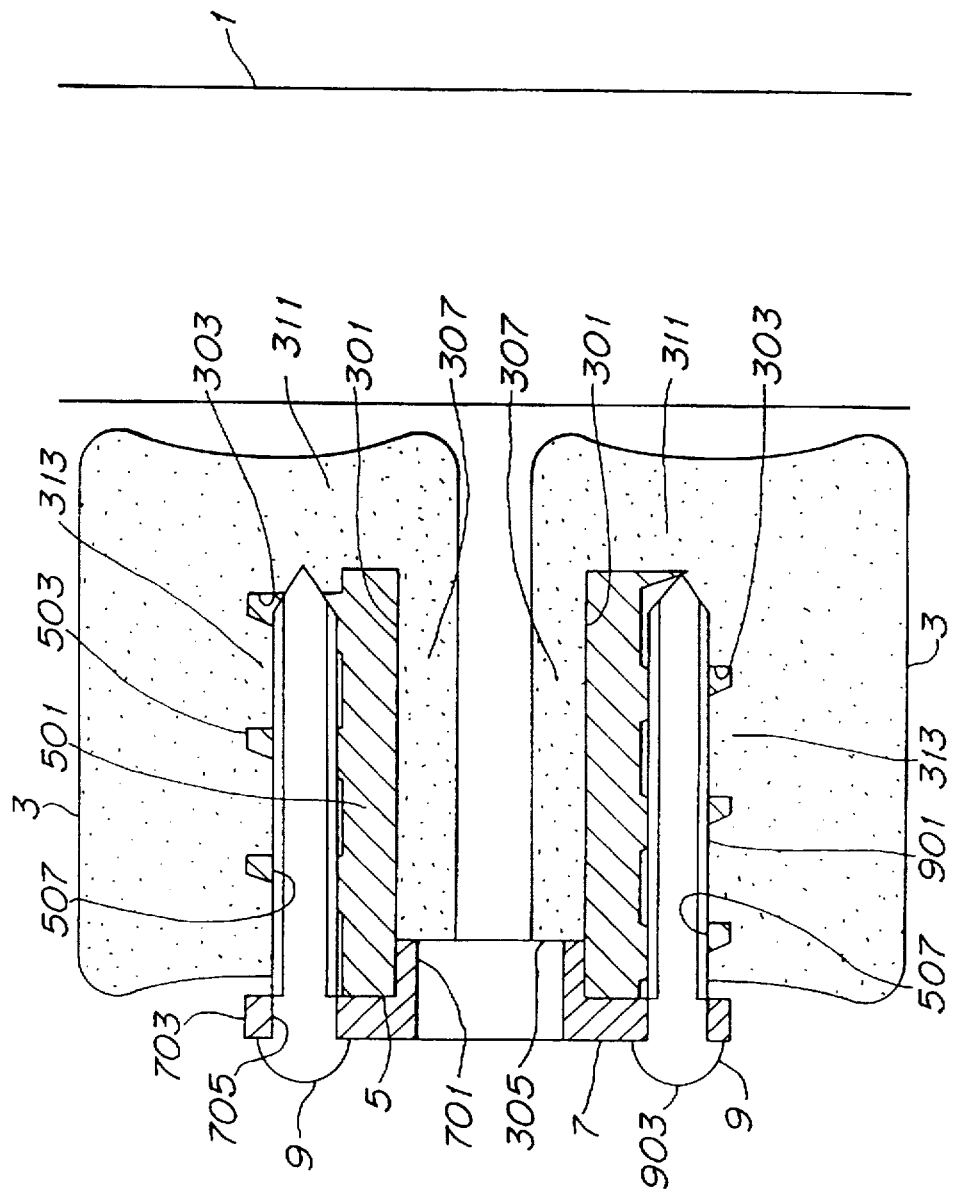
FIG. 1 is a cross-sectional view of an artificial vertebra spacer according to a first embodiment of the present invention, with an annular plate and screws as they are used to interconnect adjacent vertebrae.
Figure 2:
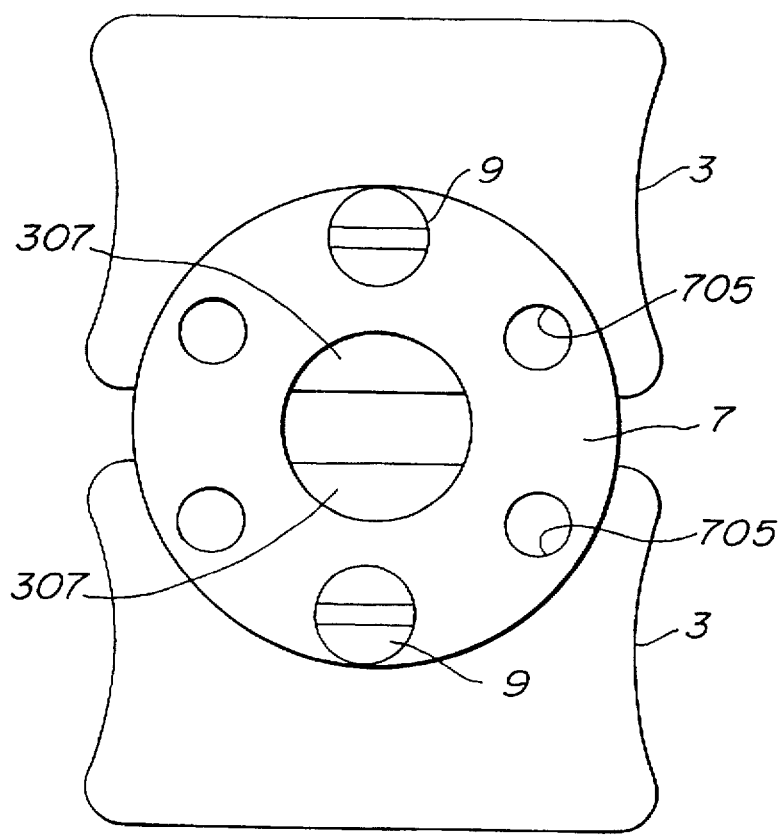
FIG. 2 is a front elevational view of the annular plate and the screws coupled to the artificial vertebra spacer.

The present invention is particularly useful when embodied in an artificial vertebra spacer for spacing and interconnecting adjacent vertebrae after a faulty intervertebral disk has been removed from cervical vertebrae or lumbar vertebrae of a vertebral column, as shown in FIGS. 1 and 2.

As shown in FIGS. 1 and 2, a vertebral column has a spinal cord 1 and a vertical array of vertebrae 3. In FIGS. 1 and 2, a faulty intervertebral disk has been removed from between two adjacent vertebrae 3. An artificial vertebra spacer 5 according to the present invention is embedded in and bridges the space between the adjacent vertebrae 3, and is fixed to the vertebrae 3 by an annular plate 7 and two screws 9.

Figure 3:
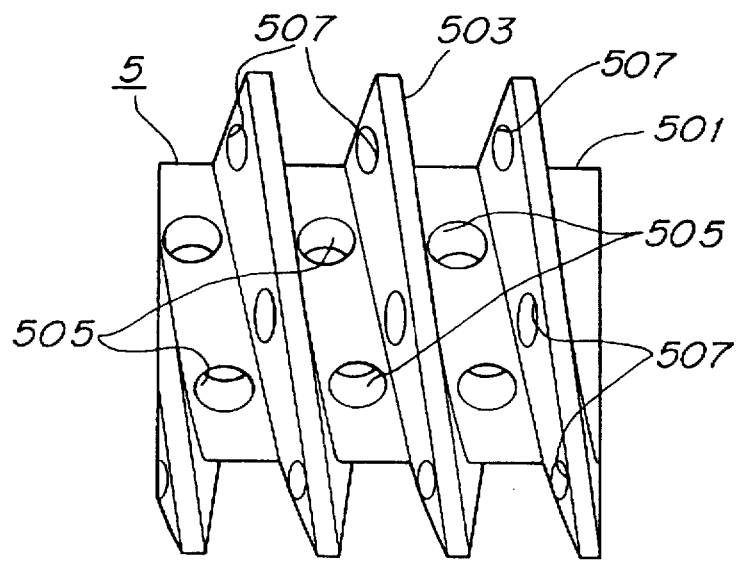
FIG. 3 is a side elevational view of the artificial vertebra spacer.
Figure 4:
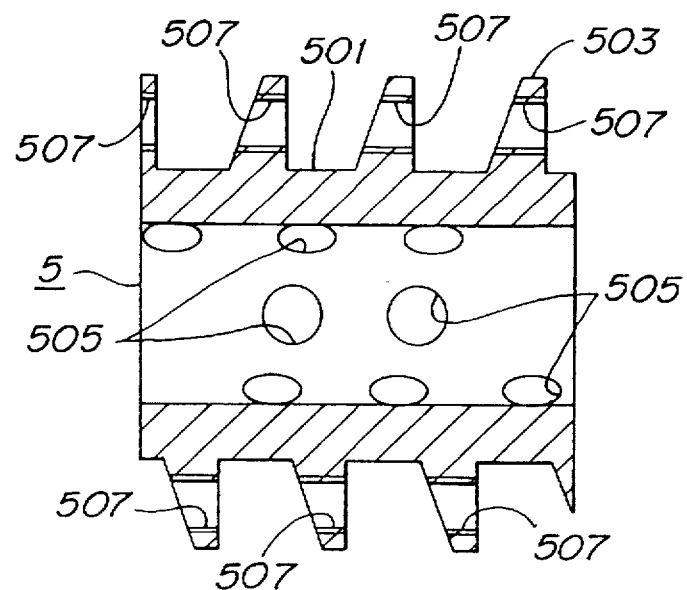
FIG. 4 is a cross-sectional view of the artificial vertebra spacer.
Figure 5:
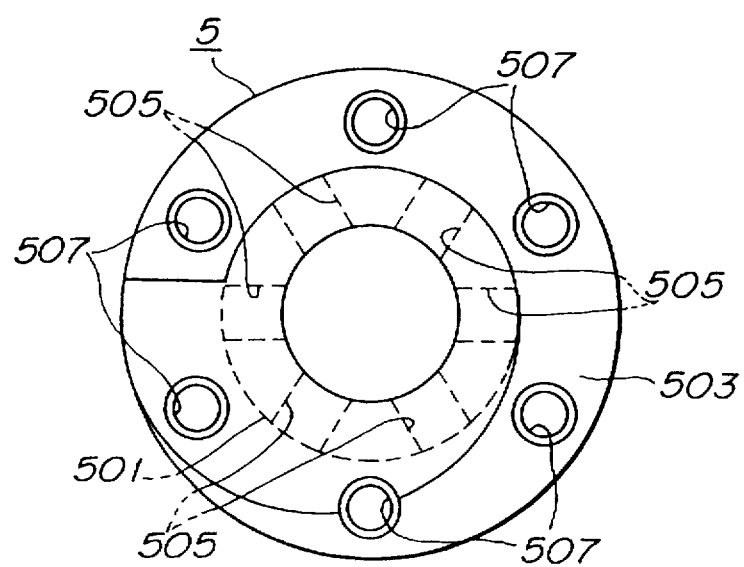
FIG. 5 is a front elevational view of the artificial vertebra spacer.

As shown in FIGS. 3, 4, and 5, the artificial vertebra spacer 5 comprises a hollow cylindrical member 501 and a helical screw thread or rib 503 of trapezoidal cross section disposed integrally on and extending helically around the hollow cylindrical member 501. When the artificial vertebra spacer 5 is embedded in the adjacent vertebrae 3, it has an outer end exposed on front surfaces of the vertebrae 3. As shown in FIG. 1, the hollow cylindrical member 501 is of such a length that when it is embedded in the adjacent vertebrae 3, its inner distal end terminates short of the rear surfaces of the vertebrae 3 which face the spinal cord 1, leaving vertebral portions 311 between the inner end of the hollow cylindrical member 501 and the rear surfaces of the vertebrae 3. The hollow cylindrical member 501 has a plurality of radial holes 505 defined therein which communicate between inner and outer circumferential surfaces of the hollow cylindrical member 501.

As shown in FIG. 5, the helical screw thread 503 has six screw holes 507 angularly spaced at equiangular intervals in the circumferential direction. The screw holes 507 extend parallel to the axis of the hollow cylindrical member 501.

The artificial vertebra spacer 5 is made of a titanium alloy and coated with a calcium phosphate compound which is porous hydroxy apatite in the illustrated embodiment.

Figure 6:
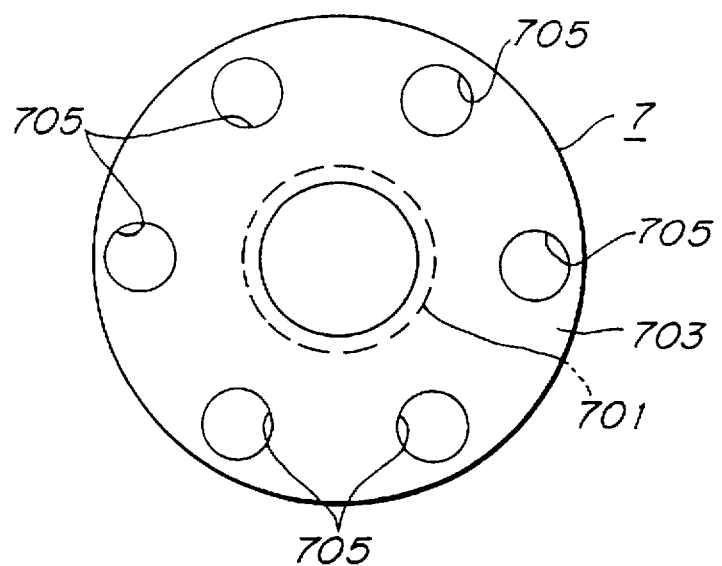
FIG. 6 is a front elevational view of the annular plate.
Figure 7:
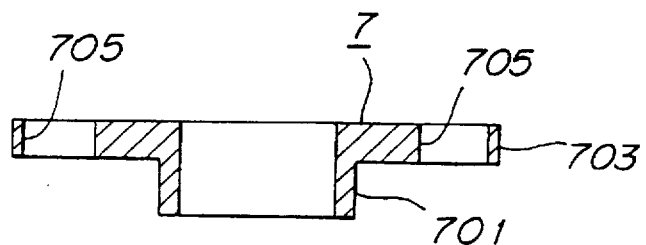
FIG. 7 is a cross-sectional view of the annular plate.

As shown in FIGS. 6 and 7, the annular plate 7 comprises a smaller-diameter tubular member 701 and a circular flange 703 extending radially outwardly from an axial end of the tubular member 701.

The tubular member 701 has an outside diameter small enough to fit in the hollow cylindrical member 501. The circular flange 703 has an outside diameter which is substantially the same as the outside diameter of the helical screw thread 103. The circular flange 703 has six insertion holes 705 angularly spaced at equiangular intervals in the circumferential direction. The insertion holes 705 are identical in size to the screw holes 507 in the helical screw thread 503, and are alignable respectively with the screw holes 507.

The annular plate 7 is made of a titanium alloy and coated with a calcium phosphate compound which is porous hydroxy apatite in the illustrated embodiment.

Each of the screws 9 comprises a shank 901 and a head 903 on one end of the shank 901, as shown in FIG. 1.

The shank 901 of each screw 9 has an externally threaded surface, and can be threaded into the screw holes 507 in the helical screw thread 103. The shank 901 of each screw 9 has a length such that it can be inserted through one of the insertion holes 705 all the way into an aligned one of the screw holes 507, with its tip end reaching the distal end of the artificial vertebra spacer 5 and the head 9 held against the outer surface of the annular plate 7.

Each of the screws 9 is made of a titanium alloy and coated with a calcium phosphate compound which is porous hydroxy apatite in the illustrated embodiment.

A process of interconnecting two adjacent vertebrae 3 positioned superiorly and inferiorly a removed faulty intervertebral disk in spaced-apart relationship will be described below with reference to FIG. 1.

First, an annular groove 301 which is of such a size as to snugly receive the hollow cylindrical member 501 is formed jointly in the two adjacent vertebrae 3. A helical groove 303 which is of such a size as to snugly receive the helical screw thread 503 is also formed jointly in the two adjacent vertebrae 3 radially outwardly of and in communication with the annular groove 301.

Then, two small holes, which are smaller in diameter than the screw holes 507 and as long as the screws 9, are formed respectively in the vertebrae 3. These two small holes extend across the helical groove 303, and are diametrically oppositely positioned in alignment with diametrically opposite two of the six screw holes 507, which are lined up with the spinal cord 1 after the artificial vertebra spacer 5 is rotated to insert the hollow cylindrical member 501 and the helical screw thread 503 fully into the annular groove 301 and the helical groove 303, respectively.

Recesses 305 are formed in front confronting portions of the vertebrae 3 for receiving the tubular member 701 of the annular plate 7.

Thereafter, the hollow cylindrical member 501 and the helical screw thread 503 are axially inserted into the annular groove 301 and the helical groove 303, respectively, while the artificial vertebra spacer 5 is being rotated. The artificial vertebra spacer 5 is continuously rotated to insert the hollow cylindrical member 501 and the helical screw thread 503 fully into the annular groove 301 and the helical groove 303, respectively, i.e., until the outer end of the artificial vertebra spacer 5 projects slightly on the front surfaces of the vertebrae 3. At this stage of insertion, the vertebrae 3 have respective confronting portions 307 contiguous to the respective vertebral portions 311 and positioned within the hollow cylindrical member 501. The rotation of the artificial vertebra spacer 5 is stopped with two of the screw holes 507 being aligned with the two small holes in the respective vertebrae 3.

Then, the tubular member 701 of the annular plate 7 is fitted in the hollow cylindrical member 501 and accommodated in the recesses 305, and the annular plate 7 is turned to bring the insertion holes 705 into alignment with the respective screw holes 507.

The two screws 9 are thereafter inserted through the respective insertion holes 705 and threaded into the two screw holes 507 and the aligned small holes in the vertebrae 3. The screws 9 are tightened until their heads 903 are engaged by the outer surface of the annular plate 7.

Since the artificial vertebra spacer 5 is embedded in and secured to the superiorly adjacent and inferiorly adjacent vertebrae 3 and the confronting portions 307 of the vertebrae 3 are left within the hollow cylindrical member 501, the artificial vertebra spacer 5 can bear compressive forces, tensile forces, and forces normal to these compressive and tensile forces, all of which are applied to the vertebrae 3. Therefore, even when the vertebrae 3 are subjected to compressive forces, tensile forces, or forces normal to these compressive and tensile forces, the vertebrae 3 are stably held in position by the artificial vertebra spacer 5. After the artificial vertebra spacer 5 has been embedded, the bone tissue of the confronting portions 307 of the vertebrae 3 which remain positioned within the hollow cylindrical member 501 grows to the extent that the confronting portions 307 are fused to each other. Therefore, the vertebrae 3 can stably be held together.

The bone tissue of the vertebrae 3 as it grows enters the holes 505 in the hollow cylindrical member 501. Therefore, the confronting portions 307 of the vertebrae 3 which remain positioned within the hollow cylindrical member 501 and vertebral portions 313 positioned radially outwardly of the hollow cylindrical member 501 are fused to each other through the holes 505, thereby holding the vertebrae 3 stably in position. Since the coating of calcium phosphate compound on the hollow cylindrical member 501 is highly biocompatible, the bone tissue of the vertebrae 3 finds it easy to enter the holes 505, allowing easy fusion between the confronting portions 307 of the vertebrae 3 which remain positioned within the hollow cylindrical member 501 and the vertebral portions 313 positioned radially outwardly of the hollow cylindrical member 501.

The artificial vertebra spacer 5, the annular plate 7, and the screws 9 are all made of a titanium alloy and coated with a calcium phosphate compound, as described above. Thus, the artificial vertebra spacer 5, the annular plate 7, and the screws 9 are relatively light. As the calcium phosphate compound has a high bone fusion capability, the surface layers of the artificial vertebra spacer 5, the annular plate 7, and the screws 9 can well be fused to the vertebrae 3, with the result that the artificial vertebra spacer 5 can reliably be anchored to the vertebrae 3.

The mechanical strength and rigidity of the artificial vertebra spacer 5 are increased by the annular plate 7 and the screws 9 for stably holding the vertebrae 3 in place.

Figure 8:
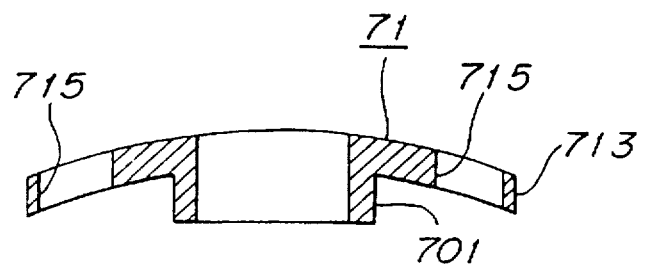
FIG. 8 is a cross-sectional view of a modified annular plate.

FIG. 8 shows a modified annular plate 71. The modified annular plate 71 comprises a partly cylindrical flange 713 extending radially outwardly from an end of a tubular member 701. The flange 713 has six insertion holes 715 defined therein at equiangular intervals. To use the modified annular plate 71, the front end surfaces of the vertebrae 3 are cut off, defining a partly cylindrical recess complementary in shape to the partly cylindrical flange 713. In use, the partly cylindrical flange 713 is snugly fitted in the partly cylindrical recess thus defined. Consequently, the modified annular plate 71 does not greatly project from the vertebrae 3.

The artificial vertebra spacer 5 may be embedded in the adjacent vertebrae 3 while a spacer or filler which has a bone fusion capability or biocompatibility is being interposed between the confronting portions 307 of the vertebrae 3.

In the illustrated embodiment, the artificial vertebra spacer 5 fixed to the vertebrae 3 is reinforced by the annular plate 7 and the screw 9 for increased mechanical strength and rigidity. However, the annular plate 7 and the screws 9 may be dispensed with.

The artificial vertebra spacer 5 may be fixed to the vertebrae 3 in various ways. For example, the hollow cylindrical member 501 may be externally threaded and may be fixedly held in position in the vertebrae 3 through threaded engagement. Alternatively, the hollow cylindrical member 501 may have a flange on an end thereof, and the artificial vertebra spacer 5 may be fixed to the vertebrae 3 by screws extending through the flange and threaded into the vertebrae 3. In the case where the annular plate 7 and the screws 9 are dispensed with, the hollow cylindrical member 501 may have an increased wall thickness or may be made of a different material for increasing the mechanical strength and rigidity of the artificial vertebra spacer 5.

Alternatively, the artificial vertebra spacer 5 may be of a hollow rectangular shape, rather than a hollow cylindrical shape.

Figure 9:
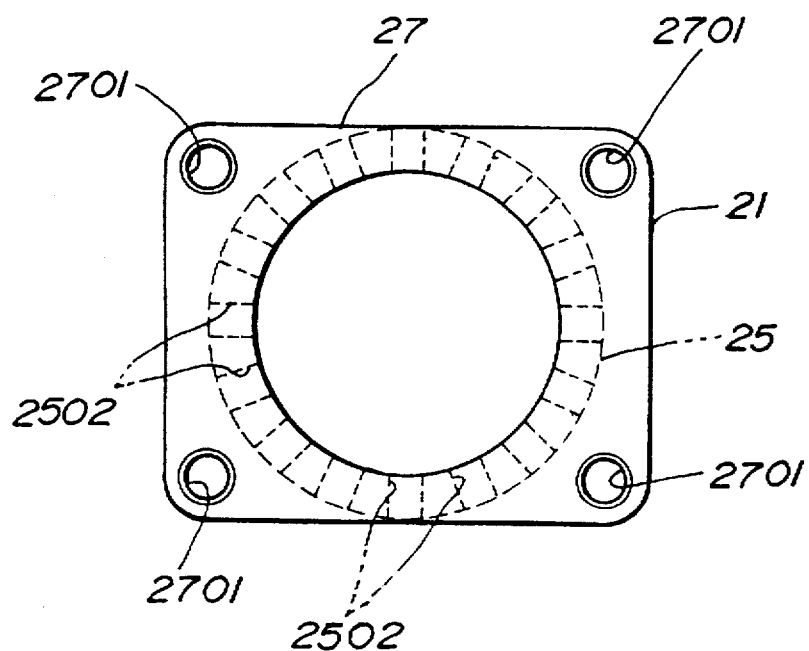
FIG. 9 is a plan view of an artificial vertebra spacer according to a second embodiment of the present invention.
Figure 10:
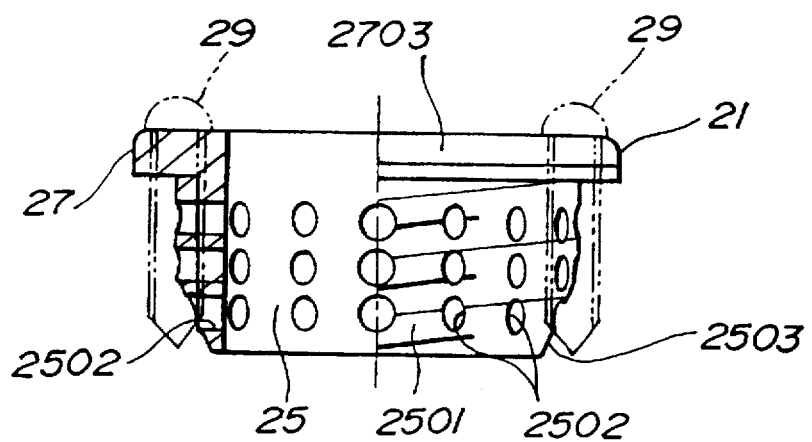
FIG. 10 is a front elevational view, partly in cross section, of the artificial vertebra spacer according to the second embodiment.

FIGS. 9 though 11 show an artificial vertebra spacer according to a second embodiment of the present invention.

The artificial vertebra spacer, denoted at 21, according to the second embodiment comprises a hollow cylindrical member 25 and a flange 27 integrally joined to an end of the hollow cylindrical member 25. The hollow cylindrical member 25 has a helical screw thread or rib 2501 on its outer circumferential surface.

The hollow cylindrical member 25 is of such a length that when it is embedded in the adjacent vertebrae 3 (see FIGS. 1 and 2), its inner distal end terminates short of the rear surfaces of the vertebrae 3 which face the spinal cord 1, leaving vertebral portions 311 between the inner end of the hollow cylindrical member 25 and the rear surfaces of the vertebrae 3. The hollow cylindrical member 25 has a plurality of radial holes 2502 defined therein which communicates between inner and outer circumferential surfaces of the hollow cylindrical member 25. The hollow cylindrical member 25 has a tapered outer surface 2503 on its end opposite to the flange 27 so that the hollow cylindrical member 25 can easily penetrate and be embedded in the vertebrae 3.

Figure 11:
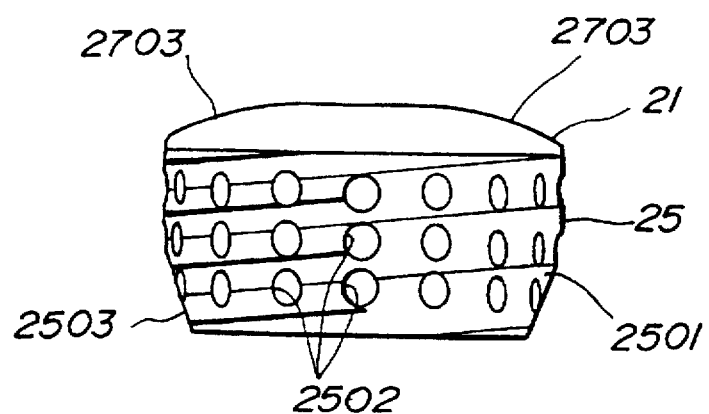
FIG. 11 is a side elevational view of the artificial vertebra spacer according to the second embodiment.

The flange 27 is of a rectangular shape with screw insertion holes 2701 defined in respective four corners thereof. As shown in FIG. 11, the flange 27 has a partly cylindrical surface 2703 on its outer side remote from the hollow cylindrical member 25.

Screws 29 can be inserted through the respective screw insertion holes 2701 threadedly into the vertebrae 3 for fastening the artificial vertebra spacer 21 to the vertebrae 3.

The artificial vertebra spacer 21 and the screws 29 are made of a titanium alloy and not coated with a calcium phosphate compound. Optionally, the artificial vertebra spacer 21 and screws 29 may be coated with a calcium phosphate compound.

Two adjacent vertebrae 3 positioned superiorly and inferiorly of a removed faulty intervertebral disk, respectively can be interconnected in spaced-apart relationship by the artificial vertebra spacer 21 as follows.

First, as with the first embodiment, an annular groove which is of such a size as to snugly receive the hollow cylindrical member 25 is formed jointly in the two adjacent vertebrae 3. Then, the artificial vertebra spacer 21 is fitted into the annular groove while it is being rotated until the artificial vertebra spacer 21 is embedded in the vertebrae 3. A helical groove which is of such a size as to snugly receive the helical screw thread 2501 may be formed jointly in the two adjacent vertebrae 3 before the hollow cylindrical member 25 is inserted into the annular groove, so that the helical screw thread 2501 will be received in the helical groove when the artificial vertebra spacer 21 is embedded in the vertebrae 3. Alternatively, no such helical groove may be formed, and the vertebrae 3 may be tapped by the self-tapping helical screw thread 2501 when the hollow cylindrical member 25 is inserted into the annular groove.

Then, four small holes, which are smaller in diameter than the screw insertion holes 2701, and as long as the screws 29, are formed in the vertebrae 3. These four small holes may be formed at the same time that the annular groove is formed in the vertebrae 3. The screws 29 are thereafter inserted through the respective screw insertion holes 2701 and threaded into the small holes in the vertebrae 3. The screws 9 are tightened until their heads are engaged by the outer surface of the flange 27.

Since the artificial vertebra spacer 21 is embedded in and secured to the superiorly and inferiorly adjacent vertebrae 3, and the vertebrae 3 have respective confronting portions 307 left within the hollow cylindrical member 25, the artificial vertebra spacer 21 can bear compressive forces, tensile forces, and forces normal to these compressive and tensile forces, all of which are applied to the vertebrae 3. Therefore, even when the vertebrae 3 are subjected to compressive forces, tensile forces, or forces normal to these compressive and tensile forces, the vertebrae 3 are stably held in position by the artificial vertebra spacer 21. After the artificial vertebra spacer 21 has been embedded, the bone tissue of the confronting portions of the vertebrae 3 which remain positioned within the hollow cylindrical member 25 grows to the extent that the confronting portions are fused to each other. Therefore, the vertebrae 3 can stably be held together.

The bone tissue of the vertebrae 3 as it grows enters the holes 2502 in the hollow cylindrical member 25. Therefore, the confronting portions of the vertebrae 3 which remain positioned within the hollow cylindrical member 25, and vertebral portions positioned radially outwardly of the hollow cylindrical member 25, are fused to each other through the holes 2502, thereby holding the vertebrae 3 stably in position.

Figure 12:
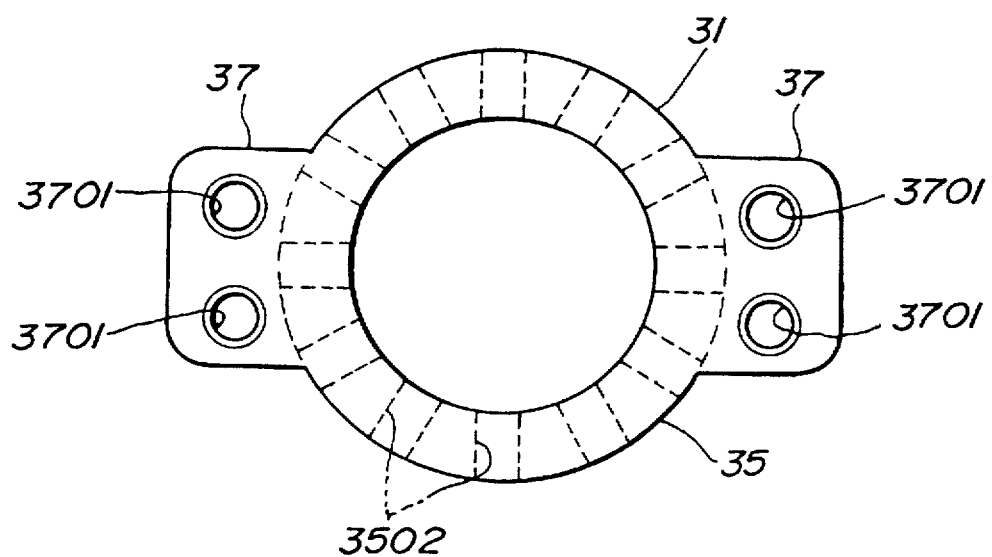
FIG. 12 is a plan view of an artificial vertebra spacer according to a third embodiment of the present invention.

An artificial vertebra spacer according to a third embodiment of the present invention will be described below with reference to FIGS. 12 through 14.

The artificial vertebra spacer, denoted at 31, differs from the artificial vertebra spacer 21 according to the second embodiment with regard to the flange joined to the hollow cylindrical member.

More specifically, the artificial vertebra spacer 31 comprises a hollow cylindrical member 35 and a pair of diametrically opposite flanges 37 integrally joined to an end of the hollow cylindrical member 35. The hollow cylindrical member 35 has a helical screw thread or rib 3501 on its outer circumferential surface, a plurality of radial holes 3502 defined therein which communicate between inner and outer circumferential surfaces of the hollow cylindrical member 35, and a tapered outer surface 3503 with its diameter which tapers progressively smaller in a direction away from the end of the hollow cylindrical member 35 with the flanges 37.

The flanges 37 project radially outwardly from diametrically opposite sides, respectively, of the hollow cylindrical member 35. Each of the flanges 37 is substantially rectangular in shape, and has two screw insertion holes 3701 defined therein near its outer distal end. As shown in FIG. 14, the artificial vertebra spacer 31 has a partly cylindrical surface 3703 on the end of the hollow cylindrical member 35 to which the flanges 37 are joined. The partly cylindrical surface 3703 blends into the outer surfaces of the flanges 37.

Figure 13:
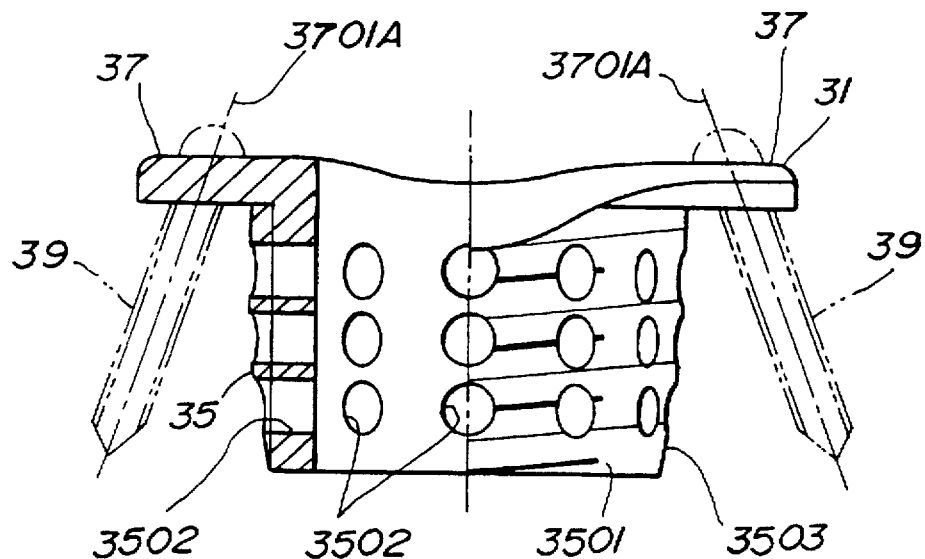
FIG. 13 is a front elevational view, partly in cross section, of the artificial vertebra spacer according to the third embodiment.
Figure 14:
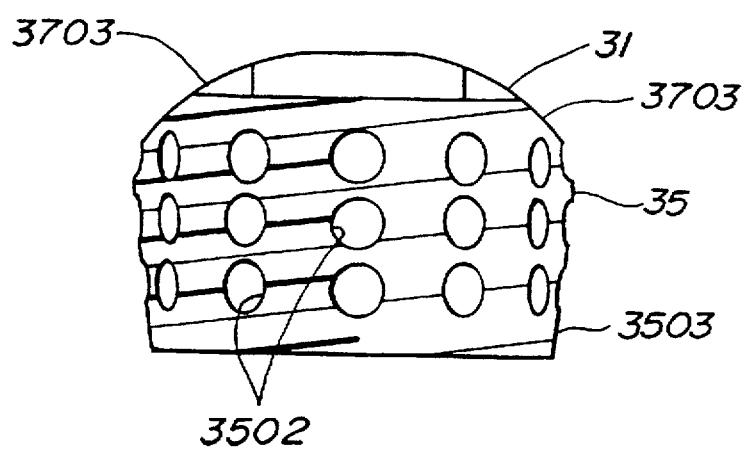
FIG. 14 is a side elevational view of the artificial vertebra spacer according to the third embodiment.

As shown in FIG. 13, the screw insertion holes 3701 have respective axes 3701A inclined with respect to the axis of the hollow cylindrical member 35, such that screws 39 inserted through the screw insertion holes 3701 to fasten the artificial vertebra spacer 31 to the vertebrae 3, have tip ends pointed obliquely away from each other.

The artificial vertebra spacer 31 and the screws 39 are made of a titanium alloy and are not coated with a calcium phosphate compound. Optionally, the artificial vertebra spacer 31 and screws 39 may be coated with a calcium phosphate compound.

Figure 15:
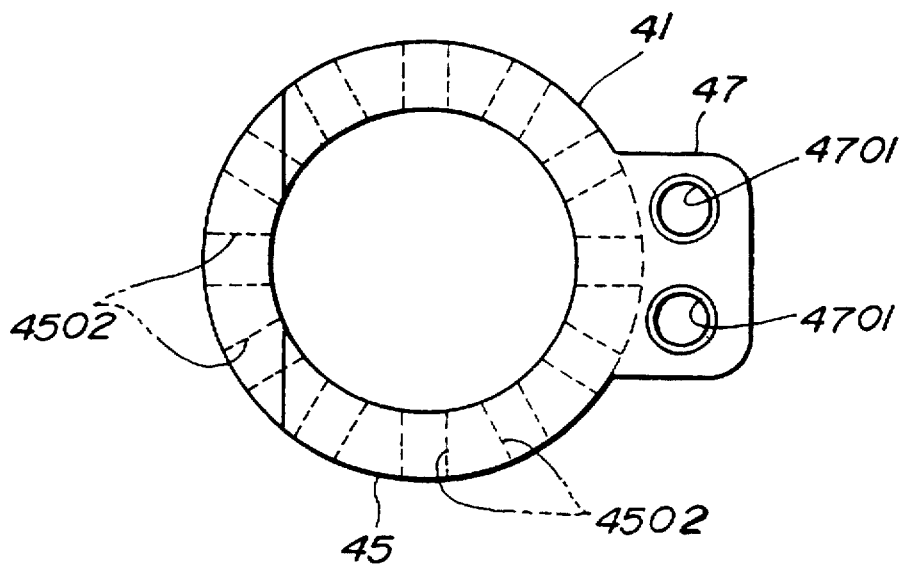
FIG. 15 is a plan view of an artificial vertebra spacer according to a fourth embodiment of the present invention.
Figure 16:
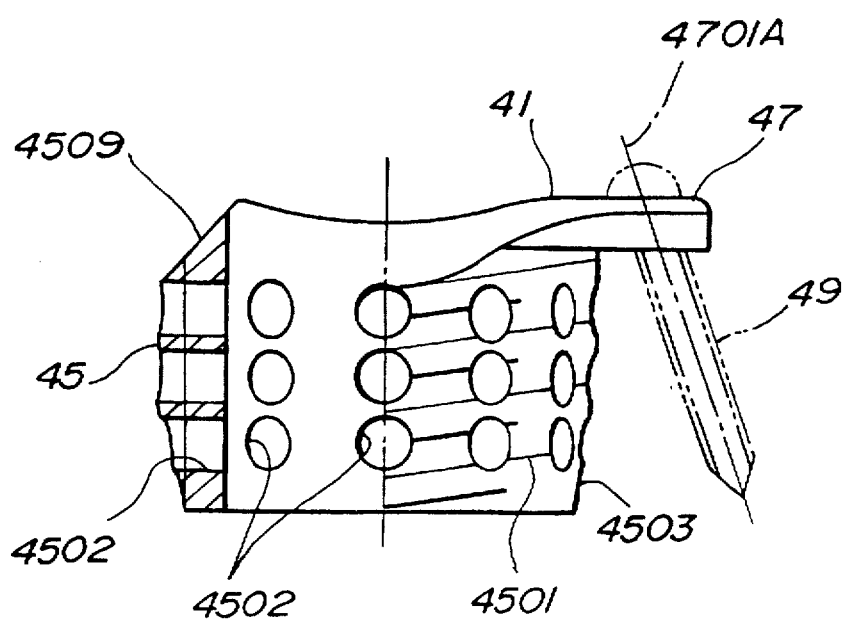
FIG. 16 is a front elevational view, partly in cross section, of the artificial vertebra spacer according to the fourth embodiment.
Figure 17:
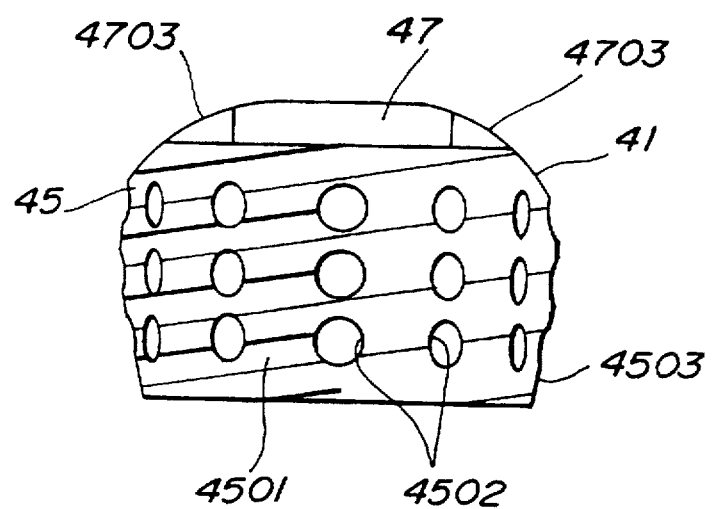
FIG. 17 is a side elevational view of the artificial vertebra spacer according to the fourth embodiment.

FIGS. 15 through 17 show an artificial vertebra spacer according to a fourth embodiment of the present invention.

The artificial vertebra spacer, denoted at 41, differs from the artificial vertebra spacer 31 according to the third embodiment, in that the artificial vertebra spacers 41 has a single flange.

More specifically, the artificial vertebra spacer 41, comprises a hollow cylindrical member 45 and a flange 47, integrally joined to an end of the hollow cylindrical member 35. The hollow cylindrical member 45 has a helical screw thread or rib 4501 on its outer circumferential surface, a plurality of radial holes 4502 defined therein which communicate between inner and outer circumferential surfaces of the hollow cylindrical member 45, and a tapered outer surface 4503 with a diameter which tapers progressively smaller in a direction away from the end of the hollow cylindrical member 45 with the flange 47.

The flange 47 projects radially outwardly from one side of the hollow cylindrical member 45. The flange 47 is substantially rectangular in shape, and has two screw insertion holes 4701 defined therein near its outer distal end. The screw insertion holes 4701 have respective inclined axes 4701A, so that screws 49 inserted therethrough are inclined with respect to the axis of the hollow cylindrical member 45. As shown in FIG. 17, the artificial vertebra spacer 41 has a partly cylindrical surface 4703 on the end of the hollow cylindrical member 45 to which the flange 47 is joined, the partly cylindrical surface 4703 blending into the outer surface of the flange 47.

As shown in FIG. 16, the hollow cylindrical member 35 has a beveled surface 4509, on a side thereof, that is diametrically opposite to the flange 47.

The artificial vertebra spacer 41 and the screws 49 are made of a titanium alloy and are not coated with a calcium phosphate compound. Optionally, the artificial vertebra spacer 41 and screws 49 may be coated with a calcium phosphate compound.

Although certain preferred embodiments of the present invention have been shown and described in detail, it should be understood that various changes and modifications may be made therein without departing from the scope of the appended claims.

What is claimed is:

1. An artificial vertebra spacer comprising:

a hollow cylindrical member sized to be embedded in two adjacent vertebrae;

screw means, provided on an outer circumferential surface of said hollow cylindrical member, for connecting said hollow cylindrical member with said two adjacent vertebrae by threadably engaging said two adjacent vertebrae;

fixing means for fixing said hollow cylindrical member to said vertebrae;

wherein said hollow cylindrical member further comprises a substantially rectangular flange portion at one end thereof and said flange portion is provided with at least one hole, and wherein said fixing means comprises at least one screw passing through said at least one hole.

2. An artificial vertebra spacer according to claim 1, wherein said hollow cylindrical member is made of metal.

3. An artificial vertebra spacer according to claim 1, wherein said hollow cylindrical member has a plurality of holes which extend in a radial direction of said hollow cylindrical member.

4. An artificial vertebra spacer according to claim 1, wherein said at least one hole comprises a longitudinal axis which is inclined at an angle with respect to a longitudinal axis of said hollow cylindrical member.

5. An artificial vertebra spacer comprising:

a hollow cylindrical member sized to be embedded in two adjacent vertebrae;

a screw, provided on an outer circumferential surface of said hollow cylindrical member, configured to connect said hollow cylindrical member with said two adjacent vertebrae by threadably engaging said two adjacent vertebrae;

a fixing mechanism configured to fix said hollow cylindrical member to said vertebrae;

wherein said hollow cylindrical member further comprises a substantially rectangular flange portion at one end of said hollow cylindrical member, said flange portion being provided with at least one hole, and wherein said fixing mechanism includes at least one screw passing through said at least one hole.

6. An artificial vertebra spacer according to claim 5, wherein said hollow cylindrical member is metal.

7. An artificial vertebra spacer according to claim 5, wherein said hollow cylindrical member has a plurality of holes which extend in a radial direction of said hollow cylindrical member.

8. An artificial vertebra spacer according to claim 5, wherein said at least one hole comprises a longitudinal axis which is inclined at an angle with respect to a longitudinal axis of said hollow cylindrical member.

\* \* \* \* \*